United States Patent [19]

Bayless

[11] Patent Number: 4,850,977
[45] Date of Patent: Jul. 25, 1989

[54] BUTTON ACTIVATED AUTOMATIC NEEDLE SHEATH FOR DISPOSABLE SYRINGE

[76] Inventor: William B. Bayless, 5353 Chelsea, La Jolla, Calif. 92037

[21] Appl. No.: 149,419

[22] Filed: Jan. 29, 1988

[51] Int. Cl.⁴ .............................................. A61M 5/32
[52] U.S. Cl. .................................... 604/198; 604/263
[58] Field of Search ................ 604/198, 192, 187, 263

[56] References Cited

U.S. PATENT DOCUMENTS

| | | |
|---|---|---|
| 2,876,770 | 3/1959 | White . |
| 3,073,306 | 1/1963 | Linder . |
| 3,354,881 | 11/1967 | Bloch . |
| 4,139,009 | 2/1979 | Alvarez . |
| 4,573,976 | 3/1986 | Sampson et al. ..................... 604/198 |
| 4,581,025 | 4/1986 | Timmermans ....................... 604/264 |
| 4,610,667 | 9/1986 | Pedicano et al. .................... 604/192 |
| 4,631,057 | 12/1986 | Mitchell .............................. 604/198 |
| 4,654,034 | 3/1987 | Masters et al. ...................... 604/192 |
| 4,659,330 | 4/1987 | Nelson et al. ........................ 604/192 |
| 4,664,654 | 5/1987 | Strauss ................................ 604/198 |
| 4,702,738 | 10/1987 | Spencer ............................... 604/198 |
| 4,702,739 | 10/1987 | Milorad ............................... 604/198 |

*Primary Examiner*—John D. Yasko
*Attorney, Agent, or Firm*—George J. Netter

[57] ABSTRACT

A needle sheath for completely encasing the needle of a disposable syringe is provided as a slidable attachment to the end of the syringe. The sheath is spring loaded. A push-button locking mechanism keeps the sheath in its unactivated position, leaving the hypodermic needle exposed, as needed for use. After use of the syringe, activating the button-locking mechanism causes the sheath to be driven by the spring mechanism to cover the length of the needle. The end flaps of the sheath that were held apart by the hypodermic needle close inward and overlap, completely encasing the needle.

10 Claims, 2 Drawing Sheets

BUTTON ACTIVATED AUTOMATIC NEEDLE SHEATH FOR DISPOSABLE SYRINGE

BACKGROUND OF THE INVENTION

1. Field of the Invention

The present invention relates generally to improvement in syringes, and more particularly pertains to new and improved sheathing means for the hollow injection needles used with the syringes.

2. Description of the Prior Art

The medical community has come to utilize disposable instrumentation with a passion. One of the prime examples of this is the syringe, which is a medical instrument used for the injection and drawing of fluids from the body. These syringes are used once and then thrown away. The most common type of syringe utilized is a hypodermic syringe which utilizes a hypodermic needle, a hollow needle of a length sufficient to inject fluids under the skin.

Although the hypodermic disposable syringe works to the satisfaction of all concerned, a critical problem has occurred as a result of the rise in communicable diseases, such as Acquired Immune Deficiency Syndrome or AIDS, in the general populace of patients being administered by the medical profession. The potential presence of every patient administered to by a medical technician or doctor having a highly contagious disease communicable through a patient's body fluids, places the heretofore nuisance pricks from used hypodermic needles suffered by the medical and nursing profession in a much more serious light. Each inadvertent prick now has the potential of passing a highly contagious and even fatal disease to the medical professional.

Although medical professionals are highly trained, skilled workers, the care and attention with which they perform their tasks are insufficient to safeguard their health and their lives in every situation. Of most concern are the emergency trauma situations wherein a group of professionals are working on a single individual in an attempt to save his life. Such a situation invariably leads to accidental stabs with used hypodermics. Hand-manipulated needle sheaths are for the most part ignored in such emergency and highly emotionally charged situations. What is needed is a hypodermic syringe which, with a minimum of manipulation after use, encases its needle in a complete enclosure.

SUMMARY OF THE INVENTION

According to the present invention, its objects and general purpose are attained by a finger-activatable release mechanism located the the needle end of the syringe body releasing a spring-loaded sheath that is propelled the length of the hypodermic needle. The end flaps of the sheath that were retained open by the hypodermic needle when the sheath was retained in its loaded position are now free to return to their natural overlapping position, thereby completely enclosing the hypodermic needle and shielding the needle point from the external environment.

BRIEF DESCRIPTION OF THE DRAWINGS

The exact nature of this invention, as well as its object and the advantages thereof, will be readily apparent from consideration of the following specification when considered in conjunction with accompanying drawings in which like reference numerals designate like parts throughout the figures thereof and wherein.

DESCRIPTION OF THE PREFERRED EMBODIMENT

Figure 1:
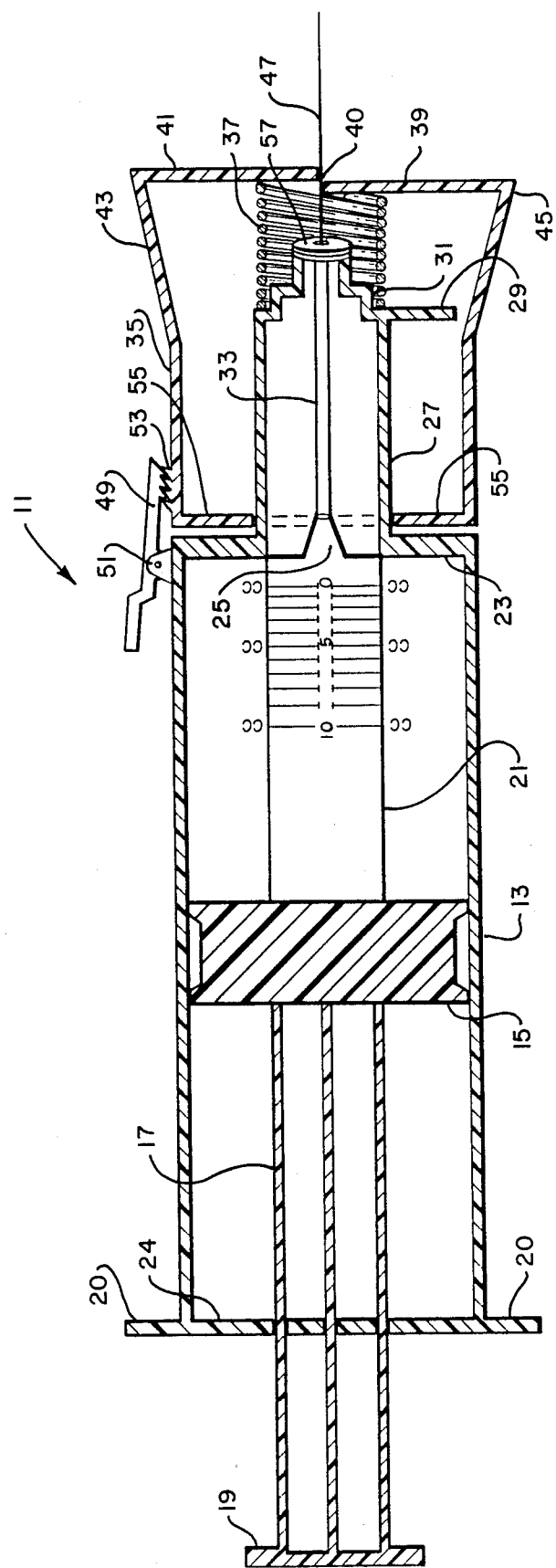
FIG. 1 is a plan view partly in section of a preferred embodiment of the invention.

FIG. 1, which illustrates a preferred embodiment of the hypodermic needle sheath of the present invention, shows a standard disposable syringe 11 utilizing the preferred sheath structure of the present invention. The hypodermic syringe 11 has a standard fluid containing chamber 13 which is closed off at one end 23 and open at the other end 24. The closed end 23 has an aperture 25 therein for the ingress and egress of fluid with respect to the chamber 13.

As is well known, this ingress and egress of fluid is caused by sealing plunger 15 moving within the chamber 13. Sealing plunger 15 is attached to a rod 17 having a thumb platform 19 at the opposite end thereof. The fluid chamber 13 has a pair of finger tabs 20 attached to the open end of the fluid chamber so that the hypodermic syringe 11 may be grasped and manipulated in one hand. Fluid level markings 21 may be etched onto the fluid chamber 13 for the purpose of illustrating the amount of fluid contained therein.

The sheath of the present invention attaches to the closed end 23 of the syringe 11. The aperture 25 in the closed end is generally adapted to receive the hypodermic needle by means of a threaded or press-fit connection, whichever is more appropriate.

The present invention contemplates that a support chamber 27 is attached to the closed end 23 of the syringe 11 to encompass the aperture 25 therein. The support chamber 27 has a fluid channel 33 therein extending through it from one end of the support chamber to the other so that fluid entering or exiting at aperture 25 can travel through channel 33 to the hypodermic needle 47 attached to the other end 57 of the support chamber 27.

The support chamber 27 may be hollow or solid as long as a fluid flow path 33 connects aperture 25 to the hypodermic needle 47 connected to the other end of the chamber 27. If the support chamber 27 is hollow, no specifically defined flow channel 33 may be necessary. The support chamber 27 is shown in FIG. 1 to be permanently in sealing engagement with the closed end 23 of fluid chamber 13 of the syringe. The support chamber 27 thereby is a part of the unitary construction of the fluid chamber 13. Fluid chamber 27 has mounted at the hypodermic needle end a stop member 29.

Mounted in slidable movement on support chamber 27 is a hollow needle sheath 35. Needle sheath 35 encases a support chamber 27 when it is located in its loaded state as shown in FIG. 1 with its end 55 next to the closed end 23 of the fluid chamber of the syringe. The syringe end of sheath 35 has an aperture therein that is sized to fit the external size and dimensions of support chamber 27 so that sheath 35 may slide along the length of support chamber 27 from fluid chamber end 23 to the stop member 29. The support member 27 may be any useful size including cylindrical, triangular or star-shaped, and the like.

At the hypodermic end of sheath 35, a slit 40 is formed for passage of the hypodermic needle 47 therethrough by pulling apart the two separated flaps 31 and 49. Flaps 39 and 41 can be separated because of the resiliency of the material used for sheath 35 and because the slit 40 extends across the end face of the sheath 35 and along its length for a short distance from the needle end, to permit the sides 43, 45 to be expanded out as shown.

The hypodermic needle 47 can be threadably attached to end 57 of the support chamber 27 thereby engaging fluid channel 33 therein and the interior of fluid chamber 13. A spring mechanism 37, which is illustrated as a coil spring, can be threadably engaged onto another portion 31 of the end of support chamber 27. Any other convenient spring mechanism may be utilized. The other end of spring 37 engages the flaps 41, 39 of sheath 35. Spring 37 is shown to be in its compressed state thereby storing energy tending to push outwardly on flaps 41 and 39 to propel the sheath 35 along the length of the hypodermic needle 47.

The force stored within spring 37 is maintained in check by a latching mechanism 49. The latching mechanism 49 is removably attached to sheath 35 by means of a grasping mechanism 53, which can be any convenient construction. Latch mechanism 49 may be disengaged from sheath 35 by a finger depression at the button end 51 of latch 49 so that latch 49 pivots out of engagement with grasping point 53. The structure illustrated for latch 49 is simply one of the many ways that such a latching function may be implemented and should not be construed as limiting the present invention. Many other latching mechanisms are equally applicable to this function.

Figure 2:
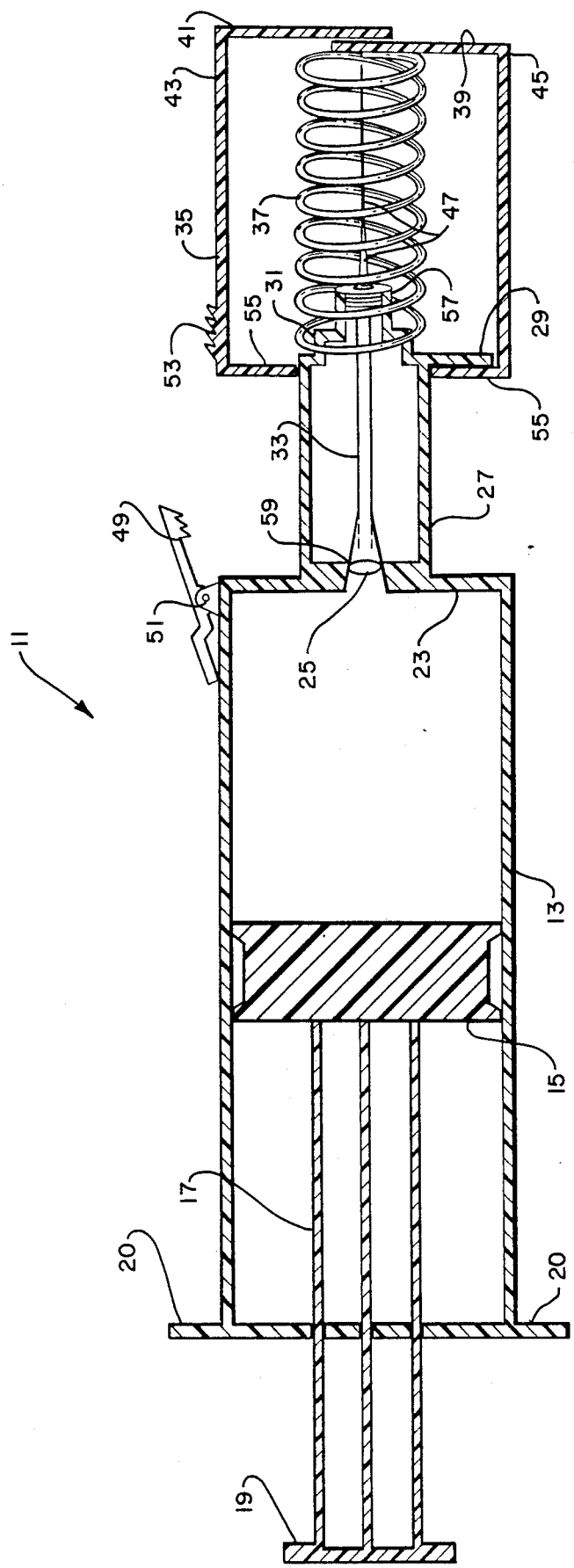
FIG. 2 is a plan view partly in section of a preferred embodiment of the invention and alternate mode.

Upon the latch 49 being disengaged, sheath 35 is immediately propelled by spring 37 along the length of support chamber 27 until its movement is impeded by stop 29. This extended position of sheath 35 is illustrated in FIG. 2. At this point, sheath 35 completely engulfs hypodermic needle 47 because the length of sheath 35 is sufficient to extend beyond the end of hypodermic needle 47. Because needle 47 is no longer extending the flaps 41 and 39 at the hypodermic needle end of sheath 35 to bend outwardly at parameters 43 and 45, flaps 41 and 39, which are designed to overlap when in their natural state completely encase the hypodermic needle 47.

FIG. 2 advantageously also illustrates an alternate preferred embodiment of the sheath mechanism of the present invention. Support chamber 27 upon which sheath 35 is slidably mounted, rather than being an integral part of fluid chamber 13 of the syringe, may be a separate member that is threadably attached to the closed end 23 of the syringe at aperture 25 by way of the threads 59 that exist at aperture 25 of the fluid chamber 13. This particular construction allows the sheath mechanism of the present invention to be retrofitted on existing hypodermic syringes having threadable ends 59 thereon.

In such a case, the latching mechanism 49 illustrated in FIG. 2 would be modified so that it is mounted on support member 27 rather than on the body of fluid chamber 13 as illustrated. By mounting latching mechanism 49 on support chamber 27 at the end which attaches to closed end 23 of the fluid chamber of the syringe, sheath 35 could be held by latch member 49 against closed end 23 of the syringe in the same way that latch member 49 as illustrated would do so.

What has been described is a novel hypodermic needle sheath which automatically completed encases the hypodermic needle of a syringe upon mere deactivation of a button-locking mechanism.

Obviously, modifications and variations of the present invention are possible in light of the above teachings. It is therefore to be understood that within the scope of the appended claims, the invention may be practiced otherwise than as specifically described.

What is claimed is:

1. A syringe having a needle sheath for completely enclosing the hypodermic after use, comprising:
    a fluid chamber open at one end and closed at the other except for a small aperture therein;
    a plunger means inserted into the open end of said fluid chamber;
    a support chamber threadably attached to said fluid chamber at the end having the small aperture therein, said support chamber having an aperture at the end opposite to the end attached to said fluid chamber and a stop member for limiting travel of the sheath;
    a hypodermic needle threadably attachable to the end of said support chamber having the small aperture and attaching at the aperture in said support chamber;
    a hollow needle sheath enclosing said support chamber, one end of said sheath sized to fit the external shape and size of said support chamber and slide there along, the other end of said needle sheath being closed except for a slit therein, overlapping flaps on the sheath at the closed end, a further slit along a portion of the sheath length, said hypodermic needle extending through the slit in said closed end when the sheath is pushed against the aperture end of said fluid chamber, and completely encased when the sheath is extended the length of said support chamber;
    a spring for driving said needle sheath along the length of said support chamber from the fluid chamber end to the needle aperture end, said spring extending around said needle between the small aperture end of said support chamber and the slit end of said sheath; and
    push-button means for releasably grasping said needle sheath and holding it against the fluid chamber end over the force of said spring means.

2. A syringe as in claim 1, in which the push-button means includes a latching mechanism which coacts with a grasping mechanism to releasably hold the needle sheath in retracted position exposing the needle.

3. The syringe of claim 1, wherein said needle sheath further comprises a resilient plastic material tending to maintain its rigid shape.

4. The syringe of claim 3 wherein said support chamber is tubular.

5. The syringe of claim 4 wherein said hollow sheath is tubular.

6. A syringe having a needle sheath for completely enclosing the hypodermic after use, comprising:
    a fluid chamber open at one end and closed at the other except for a small aperture therein;
    a plunger means inserted into the open end of said fluid chamber;
    a support chamber integrally formed with said fluid chamber physically attached to said fluid chamber at the end having the small aperture therein, said support chamber having a stop member for limiting travel of the sheath and an aperture at the end opposite to the end attached to said fluid chamber;

a hypodermic needle threadably attachable to the end of said support chamber having the small aperture and attaching at the aperture in said support chamber;

a hollow needle sheath enclosing said support chamber, one end of said sheath sized to fit the external shape and size of said support chamber and slide there along, the other end of said needle sheath being closed except for a slit therein, overlapping flaps on the sheath at the closed end, a further slit along a portion of the sheath length, said hypodermic needle extending through the slit in said closed end when the sheath is pushed against the aperture end of said fluid chamber, and completely encased when the sheath is extended the length of said support chamber;

a spring extending around said needle between the small aperture end of said support chamber and the slit end of said sheath for driving said needle sheath along the length of said support chamber from the fluid chamber end to the needle aperture end; and push-button means for releasably grasping said needle sheath and holding it against the fluid chamber end over the force of said spring means.

7. A syringe as in claim 6, in which the push-button means includes a latching mechanism which coacts with a grasping mechanism to releasably hold the needle sheath in retracted position exposing the needle.

8. The syringe of claim 6, wherein said needle sheath further comprises a resilient plastic material tending to maintain its rigid shape.

9. The syringe of claim 8 wherein said support chamber is tubular.

10. The syringe of claim 9 when said hollow needle sheath is tubular.

* * * * *